(12) United States Patent
Xu et al.

(10) Patent No.: US 10,670,526 B2
(45) Date of Patent: Jun. 2, 2020

(54) DNA SEQUENCING SYSTEM WITH STACKED BSI GLOBAL SHUTTER IMAGE SENSOR

(71) Applicant: SmartSens Technology (Cayman) Co., Limited., Shanghai (CN)

(72) Inventors: Chen Xu, Shanghai (CN); Yaowu Mo, Shanghai (CN); Zexu Shao, Shanghai (CN); Zhengmin Zhang, Shanghai (CN); Weijian Ma, Shanghai (CN)

(73) Assignee: SmartSens Technology (cayman) Co., Limited, Shanghai (CN)

( * ) Notice: Subject to any disclaimer, the term of this patent is extended or adjusted under 35 U.S.C. 154(b) by 95 days.

(21) Appl. No.: 15/911,661

(22) Filed: Mar. 5, 2018

(65) Prior Publication Data

US 2019/0271645 A1 Sep. 5, 2019

(51) Int. Cl.
*G01N 21/64* (2006.01)
*G01N 21/63* (2006.01)
*H04N 5/3745* (2011.01)
*G01N 21/17* (2006.01)
*C12Q 1/68* (2018.01)
*C12Q 1/6869* (2018.01)

(52) U.S. Cl.
CPC ....... *G01N 21/6402* (2013.01); *C12Q 1/6869* (2013.01); *G01N 21/636* (2013.01); *G01N 21/6428* (2013.01); *G01N 21/6456* (2013.01); *H04N 5/37457* (2013.01); *C12Q 1/68* (2013.01); *G01N 2021/1765* (2013.01); *G01N 2021/637* (2013.01); *G01N 2021/6415* (2013.01); *G01N 2021/6471* (2013.01); *G01N 2021/6493* (2013.01); *G01N 2201/0697* (2013.01)

(58) Field of Classification Search
CPC .......... G01N 21/6402; G01N 21/6428; G01N 21/6456; H04N 5/37457
See application file for complete search history.

(56) References Cited

U.S. PATENT DOCUMENTS

| | | | |
|---|---|---|---|
| 6,524,829 B1 * | 2/2003 | Seeger | C12Q 1/6869 435/6.11 |
| 6,731,335 B1 | 5/2004 | Kim et al. | |
| 10,477,126 B1 * | 11/2019 | Xu | H04N 5/3651 |
| 2011/0309236 A1 * | 12/2011 | Tian | H01L 27/14603 250/208.1 |

(Continued)

OTHER PUBLICATIONS

Yannick De Wit, Tomas Geurts; Title: A Low Noise Low Power Global Shutter CMOS Pixel Having Capability and Good Shutter Efficiency; Date: Unknown; pp. 1-4; Pub: Belgium.

*Primary Examiner* — Violeta A Prieto
(74) *Attorney, Agent, or Firm* — Eric Karich; Karich & Associates (57) ABSTRACT

An improved DNA sequencing system comprising a DNA sample holder residing on a stacked BSI global shutter image sensor illuminated by a pulsed laser for fluorescent illumination detection. The pulsed laser has on and off periods wherein during the laser on period a Fluorophore tag attached to a DNA sample is excited to produce fluorescence emission while the imaging system captures no illumination and during the off period the global shutter imaging system captures persistent fluorescent emission from the DNA sample and reads out an imaging signal.

13 Claims, 5 Drawing Sheets

(56) References Cited

U.S. PATENT DOCUMENTS

| | | | |
|---|---|---|---|
| 2015/0296158 A1* | 10/2015 | Mansoorian | H04N 5/374 |
| | | | 348/308 |
| 2018/0227513 A1* | 8/2018 | Keung | H01L 27/14643 |
| 2018/0227516 A1* | 8/2018 | Mo | H04N 5/3575 |
| 2018/0227523 A1* | 8/2018 | Mo | H04N 5/378 |
| 2018/0227529 A1* | 8/2018 | Mo | H04N 5/3745 |
| 2019/0273879 A1* | 9/2019 | Xu | H04N 5/3559 |

* cited by examiner

DNA SEQUENCING SYSTEM WITH STACKED BSI GLOBAL SHUTTER IMAGE SENSOR

BACKGROUND OF THE INVENTION

Field of the Invention

This invention relates generally to DNA sequencing systems, and more particularly to DNA sequencing systems with nucleotide sample holder and BSI CMOS image sensors in a stacked chip configuration with global shutter readout. A first stacked chip includes an array of light sensitive regions and structures to capture an image during DNA sequencing. A second stacked chip includes circuit elements to extract an image from the array and embedded circuit blocks to provide more efficient DNA sequence determination.

Description of Related Art

DNA sequencing is the process of determining the order of nucleotides within a DNA molecule. It includes any method or technology that is used to determine the order of the four bases—adenine, guanine, cytosine, and thymine—in a strand of DNA. The advent of rapid DNA sequencing methods has greatly accelerated biological and medical research and discovery. Knowledge of DNA sequences has become indispensable for basic biological research, and in numerous applied fields such as medical diagnosis, biotechnology, forensic biology, virology and biological systematics.

The rapid speed of sequencing attained with modern DNA sequencing technology has been instrumental in the sequencing of complete DNA sequences, or genomes of numerous types and species of life, including the human genome and other complete DNA sequences of many animal, plant, and microbial species. The first DNA sequences were obtained in the early 1970's by academic researchers using laborious methods based on two-dimensional chromatography. Following the development of fluorescence-based sequencing methods with a DNA sequencer, DNA sequencing has become easier and orders of magnitude faster.

Sanger Sequencing is a method of DNA sequencing based on the selective incorporation of chain-terminating dideoxy-nucleotides by DNA polymerase during in vitro DNA replication. Developed by Frederick Sanger and colleagues in 1977, it was the most widely used sequencing method for approximately 40 years. More recently, higher volume Sanger Sequencing has been supplanted by "Next-Gen" sequencing methods, especially for large-scale, automated genome analyses. Microfluidic Sanger Sequencing is a lab-on-a-chip application for DNA sequencing, in which the Sanger Sequencing steps (thermal cycling, sample purification, and capillary electrophoresis) are integrated on a wafer-scale chip using nanoliter-scale sample volumes. This technology generates long and accurate sequence reads, while obviating many of the significant shortcomings of the conventional Sanger Sequencing method (e.g., high consumption of expensive reagents, reliance on expensive equipment, personnel-intensive manipulations, etc.) by integrating and automating the Sanger Sequencing steps.

In its modern inception, high-throughput genome sequencing involves fragmenting the genome into small single-stranded pieces, followed by amplification of the fragments by Polymerase Chain Reaction (PCR). Adopting the Sanger Sequencing method, each DNA fragment is irreversibly terminated with the incorporation of a fluorescently labeled dideoxy chain-terminating nucleotide, thereby producing a DNA "ladder" of fragments that each differ in length by one base and bear a base-specific fluorescent label at the terminal base. Chain-termination methods have greatly simplified DNA sequencing. In dye-terminator sequencing, each of the four dideoxynucleotide chain terminators is labelled with fluorescent dyes, each of which emit light at different wavelengths. Image capture devices such as BSI CMOS image sensors provide an opportunity to image the light emitted from fluorescent dyes in a compact and cost efficient manner for use in DNA sequencing systems.

An image capture device includes an image sensor and an imaging lens. The imaging lens focuses light onto the image sensor to form an image, and the image sensor converts the light into electrical signals. The electric signals are output from the image capture device to other components of a host electronic system. The image capture device and the other components of a host electronic system form an image sensor system or imaging system. Image sensors have become ubiquitous and may be found in a variety of electronic systems, for example a mobile device, a digital camera, a medical device, or a DNA sequencing system.

A typical image sensor comprises a number of light sensitive picture elements ("pixels") arranged in a two-dimensional array. Such an image sensor may be configured to produce a color image by forming a color filter array (CFA) over the pixels. The technology used to manufacture image sensors, and in particular, complementary metal-oxide-semiconductor ("CMOS") image sensors, has continued to advance at great pace. For example, the demands of higher resolution and lower power consumption have encouraged the further miniaturization and integration of these image sensors. However, miniaturization has come with the loss of pixel photosensitivity and dynamic range which require new approaches to mitigate.

With the decreased pixel size, the total light absorption depth within the substrate becomes insufficient for some light, especially long-wavelength light. This becomes a particular problem for image sensors using backside illumination (BSI) technology wherein the image light is incident upon the backside of the sensor substrate. In BSI technology the sensor Silicon substrate may be only two microns (micrometers) thick which is adequate to absorb blue light but very inadequate to absorb red light which may require ten microns of thickness to be fully absorbed.

It is known to form a given image sensor as a so-called stacked BSI image sensor. In a typical arrangement of this type, photodiodes or other light sensitive elements of the pixel array are formed in a first semiconductor die or substrate, while associated readout circuitry for processing signals from the photosensitive elements is formed in a second semiconductor die or substrate that directly overlies the first semiconductor die or substrate. These first and second semiconductor die or substrates are more generally referred to herein as sensor and circuit chips, respectively. More precisely, the first and second semiconductor die are formed alongside many other like die on the first and second semiconductor wafers which are stacked, after aligning associated inter-wafer electrical interconnects, and diced or cut into a stacked assembly of commonly called semiconductor chips.

When reference is made to stacking two chips it is understood that in common practice two wafers are stacked and diced into chips that remain stacked to form an electrical system such as a stacked image sensor. It is however possible to stack individual chips taken from a first wafer on to other chips still in wafer form or even to stack two chips. Also the inter-wafer electrical interconnects coupling the sensor and circuit wafers may be referred to as inter-chip interconnects while intra-wafer interconnects and intra-chip interconnects refer to interconnections formed among devices residing on the same wafer and chip respectively. An advantage associated with this arrangement includes that the resulting image sensor system occupies a reduced area compared with not stacked arrangements. An additional advantage is that different manufacturing methods and materials may be used to fabricate each chip allowing independent optimizations to be employed.

An opportunity for improvement of DNA sequencing systems arises when backside image sensors are configured in a stacked chip arrangement and operated in global shutter readout mode to image fluorescent dyes. The present invention fulfills these needs and provides further advantages as described in the following summary.

SUMMARY OF THE INVENTION

The present invention teaches certain benefits in construction and use which give rise to the objectives described below.

An improved DNA sequencing system has among its components a backside illuminated (BSI) image sensor, a transparent DNA sample holder test chip positioned immediately above the imaging surface, a pulsed laser beam source for illuminating a DNA sample, and readout and image processing circuits stacked on the other parallel surface of the image sensor substrate. A DNA sample is combined with fluorescent tagging material and introduced into the DNA sample holder test chip which places the sample between the laser source and the BSI imaging array. The DNA sample is exposed to the laser light and the attached fluorescent tag material emits its characteristic light which is detected by the imaging array. The circuits stacked on the non-imaging side of the image sensor immediately analyze the fluorescent light signal.

A primary objective of the present invention is to provide an improved DNA sequencing system having advantages not taught by the prior art. For example, to provide a DNA sequencing system with fewer component parts and thereby reduce system complexity and cost. One specific example is the elimination of a long pass filter over the image sensor to filter out the laser light used for excitation. Another example is the elimination of a dichroic mirror often used in prior art DNA sequencer systems to separate the incident laser light from fluorescent signal light. With the elimination of such example components the sample holder and the image sensor may be brought closer to each other and thereby dramatically increase fluorescence emission detection capability.

An additional objective of the present invention is to provide a DNA sequencing system that utilizes a global shutter image sensor readout mode to effect separation between a fluorescent emission radiation signal and a laser excitation radiation, both of which may be incident upon the imaging array.

Another objective of the present invention is to provide a DNA sequencing system which incorporates a BSI image sensor with a set of circuits stacked on it which may include for example, an embedded FPGA, a GPU core, an ARM core and I/O and PLL circuits.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention.

DETAILED DESCRIPTION OF THE INVENTION

The above-described drawings illustrate the invention, an improved DNA sequencing system, or more generally an apparatus for identifying fluorophore tagged nucleotide bases. The system includes a DNA sample holder residing on a stacked BSI image sensor with a pulsed laser and a global shutter readout for fluorescent illumination detection. The pulsed laser has on and off periods wherein during the laser on period a fluorescent die attached to a DNA sample is excited while the global shutter imaging system is configured to capture no illumination and during the laser off period the global shutter imaging system is configured to capture fluorescent illumination from the DNA sample. Various embodiments of an improved DNA sequencing system are disclosed herein. In the following description, numerous specific details are set forth in order to provide a thorough understanding of the present invention. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects. A substrate may have a front side and a back side. Any fabrication process that is performed from the front side may be referred to as a frontside process while any fabrication process that is performed from the back side may be referred to as a backside process. Structures and devices such as photodiodes and associated transistors may be formed in a front surface of a substrate. A dielectric stack that includes alternating layers of metal routing layers and conductive via layers may be formed on the front surface of a substrate.

The terms "coupled" and "connected," which are utilized herein, are defined as follows. The term "connected" is used to describe a direct connection between two circuit elements, for example, by way of a metal line formed in accordance with normal integrated circuit fabrication techniques. In contrast, the term "coupled" is used to describe either a direct connection or an indirect connection between two circuit elements. For example, two coupled elements may be directly coupled by way of a metal line, or indirectly connected by way of an intervening circuit element (e.g., a capacitor, resistor, or by way of the source/drain terminals of a transistor). In the present invention of a stacked chip arrangement the front sides of two chips may be directly connected since the electrical interconnects on each chip will most commonly be formed on the front sides of each chip. When reference is made to certain circuit elements residing within or formed in a substrate this is generally accepted to mean the circuits reside on the front side of the substrate.

Figure 1:
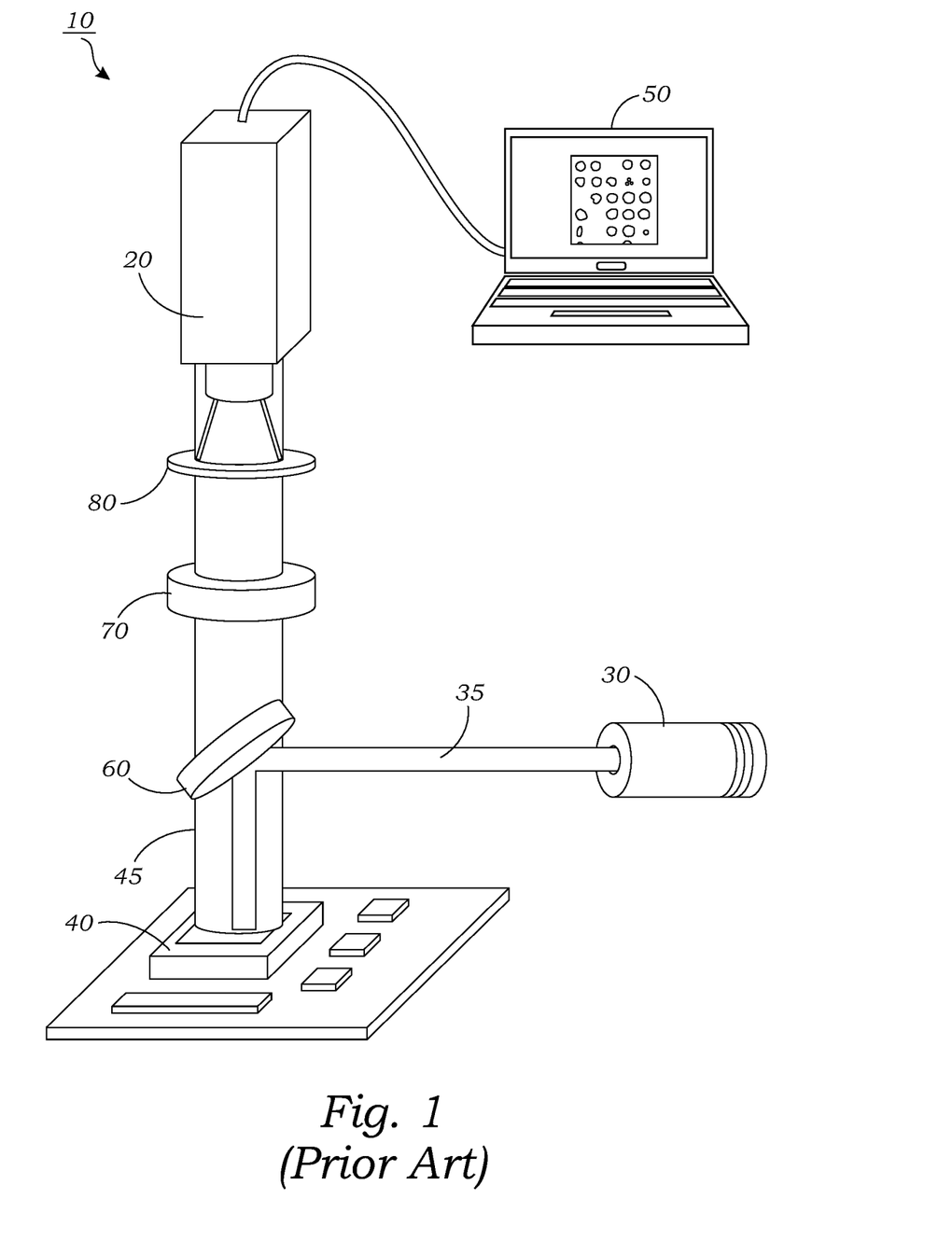
FIG. 1 is a diagram illustrating a prior art DNA sequencing system including an imaging system, a laser, a DNA sample chip and a computer analysis system.

FIG. 1 is a diagram illustrating a prior art DNA sequencing system 10, including an imaging system 20, a continuous laser 30, a DNA sample holder chip 40 and a computer analysis system 50. DNA nucleotides are made up of one sugar molecule, one phosphate molecule and one of four bases. Two of the bases are the purine bases adenine (A) and guanine (G) while the other two bases are the pyrimidine bases thymine (T) and cytosine (C). Fluorophore tags are fluorescent dyes used to measure the intensity of the dyes that bind to nucleotide bases and they selectively fluoresce when bound. When each or combinations of the bases are fluorophore-tagged and irradiated, with for example, a short wavelength laser light, they emit a characteristic wavelength light. For example, when excited by laser light with wavelengths near 488 nm, 514 nm, or 532 nm a fluorophore-tagged cytosine may emit red light, a thymine may emit green light and an adenine may emit red and green light.

As FIG. 1 illustrates, this prior art DNA sequencing system comprises a DNA sample holder chip 40 in which is placed a DNA sample to be analyzed. The DNA sample may be prepared with Fluorophore tags which fluoresce to indicate constituent bases when illuminated appropriately. Sample holder chip 40 may be comprise a transparent material with channels disposed within it to contain and direct the flow of a DNA sample containing media. Such channels may be microfluidic channels formed within the sample holder. Laser 30 is a source of intense continuous electromagnetic radiation 35, typically in the visible or infrared spectrum although alternative wavelengths may be used, whose output beam is directed onto the DNA sample by dichroic mirror 60. The dichroic mirror 60 is a mirror with significantly different reflection or transmission properties at two different wavelengths or wavelength bands. In this instance the two different wavelengths are the wavelength of the laser radiation and the wavelength of the fluorescence emission of the Fluorophore tag. The dichroic mirror 60 directs radiation 35 from laser 30 onto sample holder 40 by reflection. The DNA sample held within sample holder 40 may fluoresce upon being illuminated by laser radiation 35 and create fluorescence emission radiation 45 which exits sample holder 40 in all directions. A portion of fluorescence emission radiation 45 may travel by transmission through dichroic mirror 60 and filter 70 and lens 80 into imaging system 20. The DNA sample illumination by the laser 30 and fluorescence radiation detection by imaging system 20 may occur simultaneously since laser radiation 35 is prevented from entering imaging system 20 by dichroic mirror 60 and filter 70.

The dichroic mirror 60 may be an expensive component to fabricate due to often narrow and close reflection and transmission band requirements of such prior art systems. Also, imaging system 20 may be responsive to radiation 35 from laser 30, as well as radiation other than fluorescence radiation 45, and this may require filter 70 to be a narrow band filter. Narrow band filters typically are more expensive than wide band filters. The DNA sequencing system's capability to detect and measure fluorescence in the sample is limited by the system design requirements necessitating the placement of mirror 60 and filter 70 and lens 80 between sample holder 40 and imaging system 20. The greater the distance between the sample and the imaging system the weaker is the radiation available to be detected. An improved DNA sequencing system would have fewer components to reduce cost and less distance between the sample under examination and the imaging system to increase capability.

Figure 2:
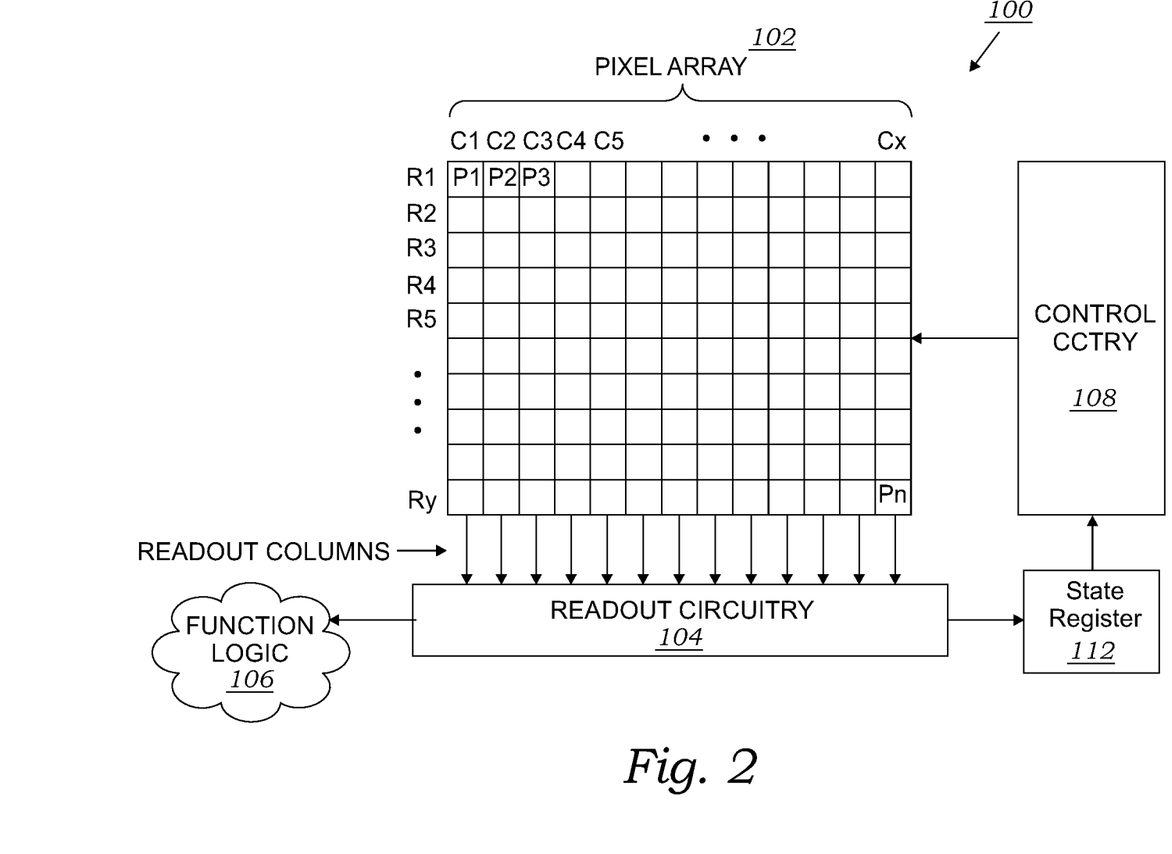
FIG. 2 is a diagram illustrating one example of an imaging system component of a DNA sequencing system.

FIG. 2 is a diagram illustrating one example of an imaging system component 100 of an example DNA sequencing system with features in accordance with the teachings of the present invention. As shown in the depicted example, the imaging system 100 includes pixel array 102 coupled to control circuitry 108 and readout circuitry 104, which is coupled to function logic 106. The control circuitry 108 and the readout circuitry 104 are in addition coupled to a state register 112. In one example, the pixel array 102 is a two-dimensional (2D) array of image sensor pixels (e.g., pixels P1, P2 . . . , Pn). As illustrated, each pixel is arranged into a row (e.g., rows R1 to Ry) and a column (e.g., column C1 to Cx) to acquire image data of a person, place, object, etc., which can then be used to render a 2D image of the person, place, object, etc. In one example, after each pixel has acquired its image data or image charge, the image data is readout by the readout circuitry 104 using a readout mode specified by the state register 112 and then transferred to function logic 106. In various examples, the readout circuitry 104 may include amplification circuitry, analog-to-digital (ADC) conversion circuitry, or otherwise. The state register 112 may include a digitally programmed selection system to determine whether readout mode is by rolling shutter or global shutter. Function logic 106 may simply store the image data or even manipulate the image data by applying post image effects (e.g., crop, rotate, remove red eye, adjust brightness, adjust contrast, or otherwise). In one example, readout circuitry 104 may readout a row of image data at a time along readout column lines (illustrated) or may readout the image data using a variety of other techniques (not illustrated), such as a serial readout or a full parallel readout of all pixels simultaneously. In one example, the control circuitry 108 is coupled to the pixel array 102 to control operational characteristics of the pixel array 102. Some aspects of the operation of the control circuitry 108 may be determined by settings present in the state register 112. For example, the control circuitry 108 may generate a shutter signal for controlling image acquisition.

Two of the most common methods for reading off the image signals generated on a sensor chip are the rolling shutter mode and the global shutter mode. The rolling shutter mode involves exposing different lines of the sensor array at different times and reading out those lines in a chosen sequence. The global shutter mode involves exposing all pixels simultaneously and for the same length of time similar to how a mechanical shutter operates on a legacy "snapshot" camera. Prior art digital imaging systems have utilized either rolling shutter or global shutter readout modes.

Rolling shutter (RS) mode exposes and reads out adjacent rows of the array at different times, that is, each row will start and end its exposure slightly offset in time from its neighbor. The readout of each row follows along each row after the exposure has been completed and transfers the charge from each row into the readout node of the pixel. Although each row is subject to the same exposure time, the row at the top will have ended its exposure a certain time prior to the end of the exposure of the bottom row of the sensor. That time depends on the number of rows and the offset in time between adjacent rows. A potential disadvantage of rolling shutter readout mode is spatial distortion which results from the above. The distortion becomes more apparent in cases where larger objects are moving at a rate that is faster than the readout rate. Another disadvantage is that different regions of the exposed image will not be precisely correlated in time and appear as a distortion in the image. To improve signal to noise in the image signal final readout, specifically to reduce temporal dark noise, a reference readout called correlated double sampling (CDS) is performed prior to the conversion of each pixel charge to an output signal by an amplifier transistor. The amplifier transistor may typically be a transistor in a source-follower (SF) configuration.

Global shutter (GS) mode exposes all pixels of the array simultaneously. This facilitates the capture of fast moving events, freezing them in time. Before the exposure (integration time) begins all the pixels are reset (RST) to the same ostensibly dark level by draining all their charge. While in reset mode the pixels can accept no incident light or rather won't accumulate signal charge related to incident radiation. At the start of the exposure all of the pixels begin simultaneously to collect charge and are allowed to do so for the duration of the exposure time. At the end of the exposure each pixel transfers its signal charge simultaneously to its readout node. Global shutter mode can be configured to operate in a continuous manner whereby an exposure can proceed while the previous exposure is being readout from the readout storage nodes of each pixel. In this mode the sensor has 100% duty cycle which optimizes time resolution and photon collection efficiency. There is no artifact in the image of the period of transient readout that occurs in rolling shutter mode. Global shutter can be regarded as essential when exact time correlation is required between different regions of the sensor area. Global shutter is also very simple to synchronize with light sources or other devices. A global shutter image sensor may also include an in-pixel antiblooming gate wherein a second transfer gate is employed to reset all the photodiodes simultaneously or hold them in reset mode after transfer of the photodiode signal charge has occurred through the first transfer gate.

Global shutter mode demands that a pixel contain at least one more transistor or storage component than a pixel using rolling shutter mode. Those extra components are used to store the image charge for readout during the time period following simultaneous exposure. When in-pixel capacitors are used to store the image charge, as opposed to using reverse biased diodes, the device may be referred to as a voltage domain global shutter. Voltage domain global shutter pixels may be less impacted by dark current and stray light. Again in order to improve signal to noise in the image signal a reference readout (e.g., CDS) is required not only to be performed prior to the conversion of each pixel charge to an output signal by an amplifier transistor but also prior to the transfer of the pixel charge to the extra components of the pixel used to store the image charge during readout.

In summary, rolling shutter can deliver the lowest read noise and is useful for very fast streaming of data without synchronization to light sources or peripheral devices. However it carries risk of spatial distortion especially when imaging relatively large, fast moving objects. There is no risk of spatial distortion when using global shutter and when synchronizing to fast switching peripheral devices it is relatively simple and can result in faster frame rates.

In the example imaging system component 100 of an example DNA sequencing system with features in accordance with the teachings of the present invention the shutter signal is a global shutter signal for simultaneously enabling all pixels within pixel array 102 to simultaneously capture their respective image data during a single acquisition window.

Real-time image processing is difficult to achieve. This is due to several factors such as the large data set represented by an image and the complex operations which may need to be performed on the image. At real-time video rates of 30 frames per second a single operation performed on every pixel of a color image can equate to tens of millions of operations per second. Many image processing applications require that several operations be performed on each pixel in the image resulting in an even larger number of required operations per second. Typically an image signal processor (ISP) is implemented within the imaging system for this purpose. It may provide demosaicing to determine which color each pixel represents and to interpolate regions at and near pixels. It also may control autofocus, exposure, and white balance for the imaging system. Recently correcting for lens imperfections like vignetting or color shading imparted by the imperfect lens system has been added, along with things like High Dynamic Range (HDR) recombining, noise reduction, other filtering, face or object detection. It may also provide focus assembly control if needed. ISPs typically have an embedded CPU (Central Processing Unit) to execute its required functions. The ISP may be included onboard the circuit wafer or as an added discrete chip. The circuit wafer may also include a GPU (Graphics Processing Unit) to speed up required information processing and or an FPGA (Field Programmable Gate Array) to facilitate customizing programmed instructions.

Figure 3:
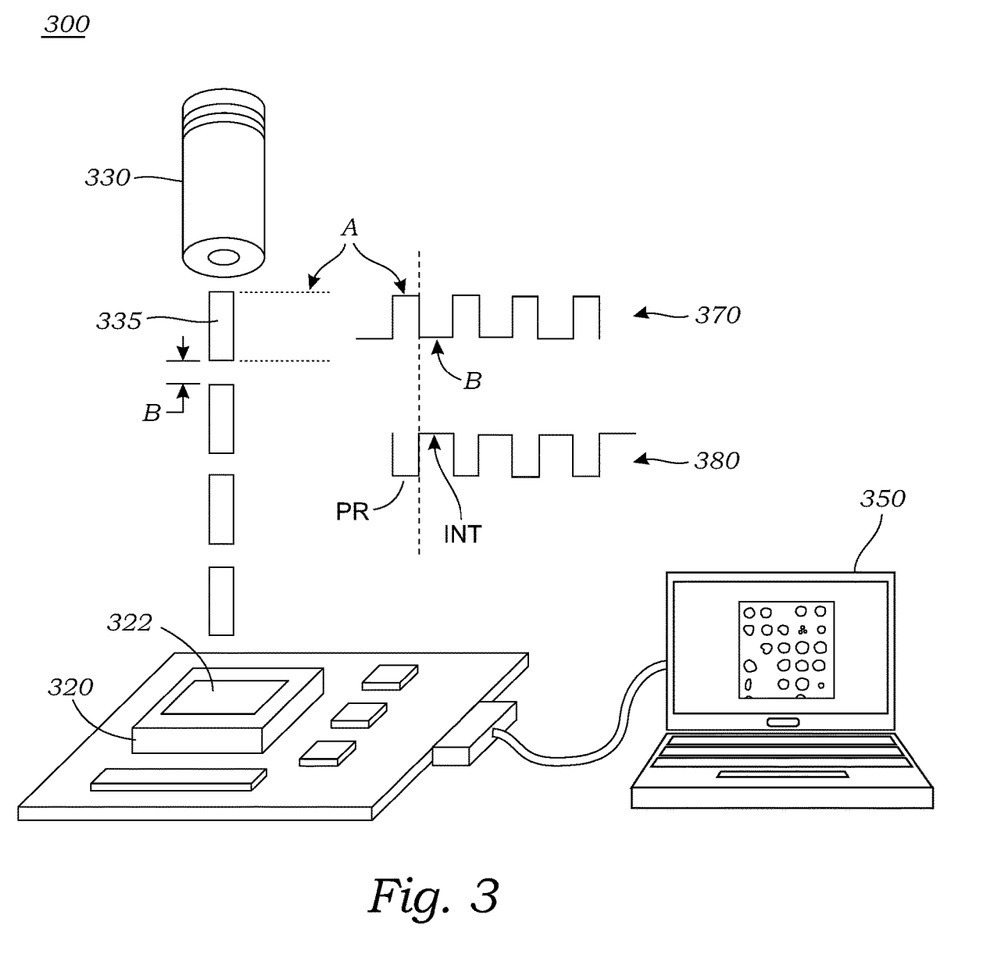
FIG. 3 is a diagram illustrating one example of a DNA sequencing system.
Figure 4:
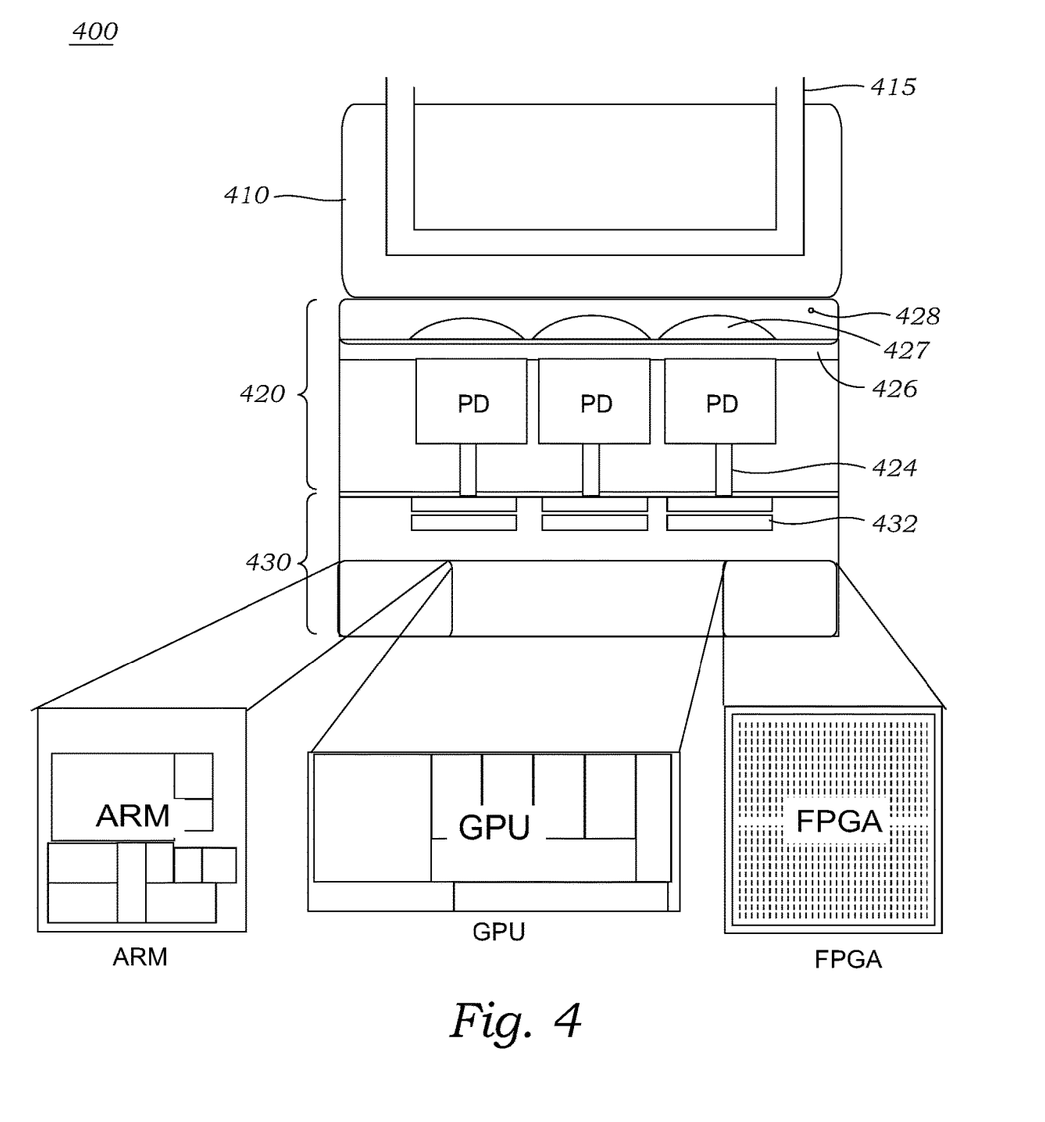
FIG. 4 is a cross section diagram illustrating one example of an imaging system component of an example DNA sequencing system.

FIG. 3 is a diagram illustrating one example of a DNA sequencing system 300 with features in accordance with the teachings of the present invention. In contrast to the prior art DNA sequencing system illustrated in FIG. 1, an imaging system 320 of the present system 300 is disposed below a DNA sample holder 322. FIG. 4 provides further detail of the sample holder and imaging system and will be described later in this application. The imaging system comprises a backside illuminated (BSI) CMOS image sensor oriented to image light incident from the DNA sample holder. The BSI image sensor further comprises a global shutter exposure integration and readout wherein all pixels are simultaneously reset and allowed to integrate incident radiation for an exposure period followed by a signal transfer and readout during a non-exposure period. FIG. 3 illustrates laser source 330 producing intense pulsed electromagnetic radiation 335 which illuminates the sample holder during an ON period A and does not illuminate the sample holder during an OFF period B. The laser illumination ON and OFF periods are illustrated in FIG. 3 by trace 370. When the sample holder is illuminated by laser radiation 335, a Fluorophore tagged DNA fragment will begin to emit fluorescent radiation unique to the Fluorophore. The Fluorophore tag may emit fluorescence radiation for a time period extending longer than the laser ON period A and extend into OFF period B. A key innovation of the invention entails firstly exposing the DNA sample to laser radiation during an ON period A while the BSI global shutter image sensor is kept in its photodiode non-exposure or reset (PR) mode during period A in order that no imaging signal be accumulated during period A. The global shutter is CLOSED in this situation. Then the laser radiation source is turned off for a time period B. The Fluorophore tag emitted fluorescence radiation may continue into period B however. Then at the beginning of time period B the image sensor photodiodes are switched into exposure integration mode (INT) followed by a charge transfer period whereby an image of the fluorescence radiation is captured by and transferred from the pixel photodiodes to the global shutter storage components. The global shutter is OPEN in this situation. At the end of time period B the global shutter image sensor is CLOSED or switched again into photodiode non-exposure or reset (PR) mode wherein no imaging occurs during the subsequent laser ON period A. Global shutter signal readout of the fluorescent radiation signal acquired during period B may occur during period A for analysis by a computer analysis system 350. Trace 380 shown in FIG. 3 illustrates the global shutter image sensor switching from CLOSED and non-exposure or reset mode PR into OPEN or exposure integration mode INT and returning to CLOSED or non-exposure or reset mode PR. As illustrated in FIG. 3 traces 370 and 380 are coordinated or aligned in time such that laser radiation only illuminates the DNA sample while the global shutter image sensor is CLOSED or in PR mode and the global shutter image sensor is OPEN and only accepts an imaging signal while the laser radiation is absent but the fluorescence radiation may persist.

This embodiment of the invention offers advantages over the prior art in that expensive components have been eliminated and the fluorescence radiation source is brought closer to the image sensor array. In particular, referencing FIG. 1, expensive components which are eliminated include the dichroic mirror 60, the narrow band filter 70, and the lens 80, discussed above. The distance between the DNA sample and image sensor is reduced from on the order of tens of centimeters to less than a millimeter. Since radiation intensity decreases by the square of the distance it travels the system sensitivity may be increased by several orders of magnitude due to the reduction of distance between the DNA sample and image sensor as provided by the invention as well as by the elimination of radiation absorbing optical elements between them.

FIG. 4 is a cross section diagram illustrating one example of an imaging system component 400 of an example DNA sequencing system (of FIG. 3) with features in accordance with the teachings of the present invention. FIG. 4 illustrates a global shutter image sensor chip 420 with DNA sequencing sample holder 410 stacked on it, with the sample chamber in view of the photodiodes PD, and circuit chip 430 stacked on its opposite side containing readout circuitry 432 which is electrically coupled to the sensor chip through inter-chip interconnects 424. DNA sequencing sample holder 410 may be formed of an optically transparent material and comprise micro-channels 415 and reservoirs to facilitate positioning a DNA sample directly above the image sensor photodiode array. Image sensor chip 420 may comprise optical filter and antireflective layer 426 to limit the radiation wavelengths admissible to the photodiodes and to reduce reflection of incident radiation at the photodiode surface. A typical filter pattern is a Bayer or color filter pattern which consists of a red, a blue and two green filters (RGGB) placed over a two by two arrangement of four photodiodes. Image sensor chip 420 may also comprise microlenses 427 placed at each photodiode site to collect, concentrate and direct incident radiation into photodiodes PD. Image sensor chip 420 may also comprise a planarization layer formed over the microlenses to facilitate a flat interface between sensor chip 420 and DNA sample holder 410. Image sensor chip 420 may most conveniently be a BSI imaging sensor as is illustrated in FIG. 4 but may also comprise a frontside illuminated (FSI) imaging sensor chip with through-substrate electrical connections used to couple to the circuit chip. Circuit chip 430 may comprise special circuit blocks for use in applying DNA detection algorithms to the signals read out from Image sensor chip 420. Special circuit blocks may be an ARM core, GPU core and FPGA core. Such special circuit blocks may all be fabricated within a single substrate also containing the image sensor readout circuits or they may be stacked on the circuit chip and electrically coupled through inter-chip interconnects. Such special circuit blocks may facilitate the use of advanced parallel processing to improve high throughput in DNA detection and analysis. They also may facilitate the incorporation of artificial intelligence capabilities. With such circuit blocks in such intimate and close proximity to the sensor chip the delays usually associated with input/output (I/O) delays may be avoided or reduced.

Figure 5:
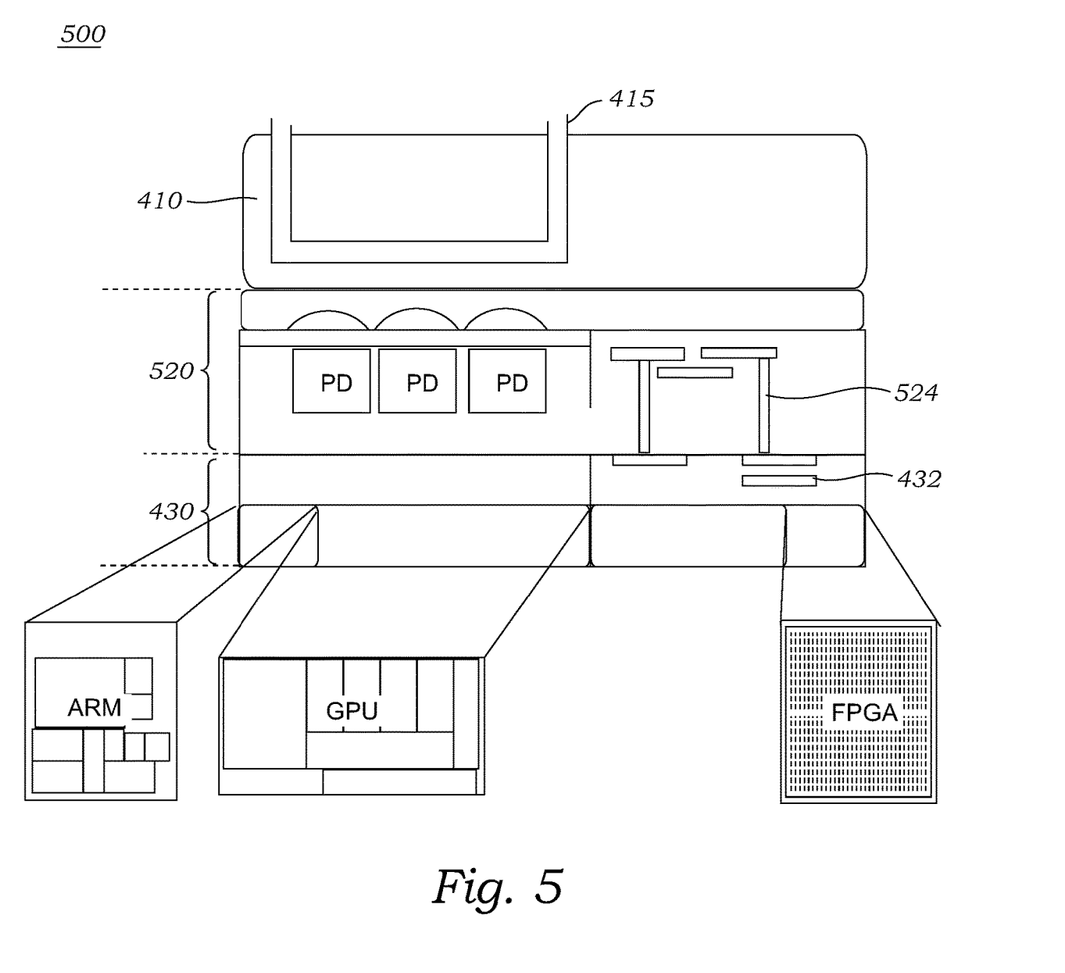
FIG. 5 is a cross section diagram illustrating another example of an imaging system component of an example DNA sequencing system.

FIG. 5 is a cross section diagram illustrating another example of an imaging system component 500 of a DNA sequencing system with features in accordance with the teachings of the present invention. The imaging system 500 is similar to imaging system 400 illustrated in FIG. 4, except that image sensor 520 comprises a frontside illuminated image sensor whose frontside circuits are electrically coupled to the underlying circuits chip 430 through silicon interconnects 524.

Reference throughout this specification to "one embodiment," "an embodiment," "one example," or "an example" means that a particular feature, structure, or characteristic described in connection with the embodiment or example is included in at least one embodiment or example of the present invention. Thus, the appearances of the phrases such as "in one embodiment" or "in one example" in various places throughout this specification are not necessarily all referring to the same embodiment or example. Furthermore, the particular features, structures, or characteristics may be combined in any suitable manner in one or more embodiments or examples. Directional terminology such as "top", "down", "above", "below" are used with reference to the orientation of the figure(s) being described. Also, the terms "have," "include," "contain," and similar terms are defined to mean "comprising" unless specifically stated otherwise. Particular features, structures or characteristics may be included in an integrated circuit, an electronic circuit, a combinational logic circuit, or other suitable components that provide the described functionality. In addition, it is appreciated that the figures provided herewith are for explanation purposes to persons ordinarily skilled in the art and that the drawings are not necessarily drawn to scale.

The above description of illustrated examples of the present invention, including what is described in the Abstract, are not intended to be exhaustive or to be limited to the precise forms disclosed. While specific embodiments of, and examples for, the invention are described herein for illustrative purposes, various equivalent modifications are possible without departing from the broader spirit and scope of the present invention. Indeed, it is appreciated that the specific example structures and materials are provided for explanation purposes and that other structures and materials may also be employed in other embodiments and examples in accordance with the teachings of the present invention. These modifications can be made to examples of the invention in light of the above detailed description. The terms used in the following claims should not be construed to limit the invention to the specific embodiments disclosed in the specification and the claims. Rather, the scope is to be determined entirely by the following claims, which are to be construed in accordance with established doctrines of claim interpretation.

What is claimed is:

1. An apparatus for identifying the presence of fluorophore tagged nucleotide bases in a sample, the apparatus comprising:
   a laser illumination source configured to emit pulses of radiation;
   an optically transparent sample holding chamber adapted to receive the sample, the sample holding chamber having a transparent top side to receive the pulses of radiation from the laser illumination source into the sample holding chamber, in order to identify the presence of the fluorophore tagged nucleotide bases by imaging the fluorescent emissions which may persist after the laser illumination ceases;
   an image sensor chip including an array of image sensing pixels with its image sensing surface stacked immediately adjacent and under the sample holding chamber and configured with in-pixel global shutter for accumulating and transferring an image signal in response to persistent fluorescent emission light incident upon the image sensor;
   a circuit chip with circuit blocks disposed within a second substrate stacked immediately adjacent and upon the other surface of the image sensor chip for coupling out the image signal through the second substrate to information processing and analysis component circuit blocks;
   wherein the image sensor global shutter pixels are open to accumulate persistent fluorescent emission and transfer out a related image signal when no laser radiation is directed into the sample holding chamber; and
   wherein the image sensor global shutter pixels are closed or in reset mode when the laser radiation pulse is directed into the sample holding chamber.

2. The apparatus of claim 1, wherein the image sensor chip comprises a backside illuminated image sensor.

3. The apparatus of claim 1, wherein the image sensor chip comprises a frontside illuminated image sensor.

4. The apparatus of claim 1, wherein on the imaging side of the image sensor is disposed an antireflective layer.

5. The apparatus of claim 4, wherein on the antireflective layer are disposed on optical filers comprising a color filter pattern.

6. The apparatus of claim 4, wherein on the antireflective layer are disposed microlenses positioned above each sensor element.

7. The apparatus of claim 5, wherein the microlenses are covered with a planarizing layer stacked immediately adjacent and under the base sample holding chamber.

8. The apparatus of claim 1, wherein the circuit blocks disposed on the second substrate comprise one of an ARM core, a GPU core and a FPGA core.

9. The apparatus of claim 1, wherein the in-pixel global shutter employs an in-pixel capacitor as the global shutter storage element.

10. The apparatus of claim 1, wherein the in-pixel global shutter employs an in-pixel anti-blooming gate for reset operation.

11. A method for identifying the presence of fluorophore tagged nucleotide bases, the method comprising the steps of:
    providing a laser illumination source configured to emit pulsed laser radiation;
    providing a sample of fluorophore tagged nucleotide bases;
    providing an optically transparent sample holding chamber that has an upper side, the sample holding chamber being adapted for receiving the sample of fluorophore tagged nucleotide bases;
    providing an image sensor chip including an array of image sensing pixels with its image sensing surface stacked immediately adjacent and under the base sample holding chamber;
    providing a circuit chip with circuit blocks disposed within a second substrate stacked immediately adjacent and upon the other surface of the image sensor chip;
    placing the sample of fluorophore tagged nucleotide bases into the sample holding chamber;
    exposing the sample in the sample holding chamber to the pulsed laser radiation such that the pulsed laser radiation passes through the sample and into the upper side of the sample holding chamber, thereby identifying the presence of fluorophore tagged nucleotide bases by imaging the release of fluorescent emissions which may persist after the pulsed laser radiation ceases;
    accumulating and transferring, via the image sensor chip configured with in-pixel global shutter, an image signal in response to fluorescent emissions emitted from the sample and incident upon the image sensor;
    coupling out the image signal through the second substrate to the circuit blocks of the circuit chip;
    closing the image sensor global shutter when the laser radiation pulse is incident on the sample;
    opening the image sensor global shutter to accumulate persistent fluorescent emission and transfer out a related image signal during the subsequent period between laser radiation pulses when no laser radiation is incident on the sample; and
    executing signal processing on the image signal within the circuit blocks to identify the presence of fluorophore tagged bases within the sample.

12. The method of claim 11, wherein the image sensing chip further comprises a backside illuminated image sensor including an array of image sensing pixels with its image sensing surface stacked immediately adjacent and under the base sample holding chamber.

13. The method of claim 11, wherein the image sensing chip further comprises a frontside illuminated image sensor including an array of image sensing pixels with its image sensing surface stacked immediately adjacent and under the base sample holding chamber.

* * * * *